(12) United States Patent
Yoshida et al.

(10) Patent No.: US 8,774,483 B2
(45) Date of Patent: Jul. 8, 2014

(54) IMAGE PROCESSING METHOD, IMAGE PROCESSING APPARATUS AND PROGRAM

(75) Inventors: Hanae Yoshida, Yokohama (JP); Michio Oikawa, Machida (JP); Tomohiro Nagao, Kashiwa (JP); Hiroki Taniguchi, Moriya (JP); Takashi Shirahata, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 216 days.

(21) Appl. No.: 13/512,817

(22) PCT Filed: Nov. 25, 2010

(86) PCT No.: PCT/JP2010/071003
§ 371 (c)(1),
(2), (4) Date: Aug. 13, 2012

(87) PCT Pub. No.: WO2011/065414
PCT Pub. Date: Jun. 3, 2011

(65) Prior Publication Data
US 2012/0308109 A1 Dec. 6, 2012

(30) Foreign Application Priority Data
Nov. 30, 2009 (JP) ................... 2009-272007

(51) Int. Cl.
*G06K 9/00* (2006.01)
*B41M 5/00* (2006.01)

(52) U.S. Cl.
USPC .............................. 382/131; 382/194; 378/29

(58) Field of Classification Search
CPC .................................. G06K 9/00; B41M 5/00
USPC ......... 382/100, 103, 106–107, 128–134, 154, 382/162, 168, 173, 181, 194, 221, 254, 274, 382/276, 285–291, 305, 312; 345/424; 378/4, 21, 29
See application file for complete search history.

(56) References Cited

U.S. PATENT DOCUMENTS

| | | | | |
|---|---|---|---|---|
| 4,751,643 A | * | 6/1988 | Lorensen et al. | 382/132 |
| 5,553,207 A | * | 9/1996 | Sekiguchi et al. | 345/424 |
| 2008/0260226 A1 | * | 10/2008 | Moriya | 382/128 |
| 2008/0267481 A1 | * | 10/2008 | Nakamura | 382/131 |

FOREIGN PATENT DOCUMENTS

| | | |
|---|---|---|
| JP | 2874445 B2 | 1/1999 |
| JP | 2005-230456 A | 9/2005 |

(Continued)

*Primary Examiner* — Seyed Azarian
(74) *Attorney, Agent, or Firm* — Volpe and Koenig, P.C.

(57) ABSTRACT

Provided is an image processing apparatus that automatically recognizes a plurality of organs to subsequently visualize the automatic recognition results in an easy-to-understand manner, and facilitate a modification of the displayed recognition results. The image processing apparatus (23) uses an image processing algorithm to perform an image processing of medical image volume data. The image processing apparatus (23) comprises an organ recognition algorithm executing unit (11) that applies an organ recognition algorithm to medical image volume data to generate and output, as an organ recognition result, structural information on the plurality of organs, and a recognition result displaying unit (32) that displays the organ recognition result. The image processing apparatus (23) comprises: a recognition result judging unit (12) that acquires, via an input device (21), judgment information on whether or not the structural information is correct enough for each of the plurality of organs to be properly recognized; and an organ recognition algorithm revising unit that acquires the judgment information from the recognition result judging unit (12), changes reference information on each organ according to the acquired judgment information and changes the organ recognition algorithm to recognize the plurality of organs using the changed reference information.

7 Claims, 9 Drawing Sheets

(56) References Cited

FOREIGN PATENT DOCUMENTS

| | | | |
|---|---|---|---|
| JP | 2008-259682 A | 10/2008 | |
| JP | 2008-259710 A2 | 10/2008 | |
| JP | 2008259710 A2 | 10/2008 | |
| JP | 2009-095644 A2 | 5/2009 | |
| JP | 2009095644 A2 | 5/2009 | |

* cited by examiner

FIG.3

|     | Examples of reference values used for organ recognition algorithm |
|-----|---|
| (1) | Diameter of coronary artery is $C_{min} - C_{max}$ [mm] |
| (2) | Diameter of ascending aorta is $UA_{min} - UA_{max}$ [mm] |
| (3) | Diameter of descending aorta is $UB_{min} - UB_{max}$ [mm] |
| (4) | $UA_{min} = F_a \times UB_{min}$ [mm] |
| (5) | $UA_{max} = F_b \times UB_{max}$ [mm] |
| (6) | $C_{min} = F_c \times UB_{min} = F_c / F_a \times UA_{min}$ [mm] |
| (7) | $C_{max} = F_d \times UB_{max} = F_d / F_b \times UA_{min}$ [mm] |

Example of human body structure used for organ recognition algorithm

Example of automatic organ recognition failure

FIG.5

Display example of automatic organ recognition result

Three-dimensional visualization of input volume data

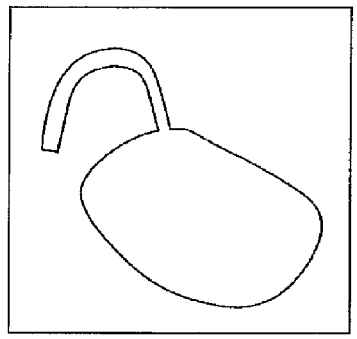

· Bone(s)
· Ascending aorta
· Coronary artery
  ⋮

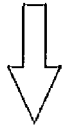

Display of automatic recognition result

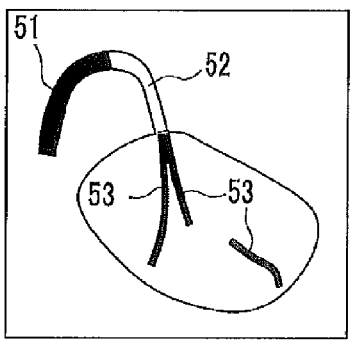

Display of recognizability

| Organ | recogniz-ability |
|---|---|
| · Bone(s) | × |
| · Ascending aorta | ○ |
| · Coronary artery | ○ |
| ⋮ | |

Judgment on recognition result

| Organ | Judgment |
|---|---|
| · Bone(s) | ✓ |
| · Ascending aorta | |
| · Coronary artery | |
| ⋮ | |

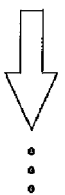

Display of automatic recognition result

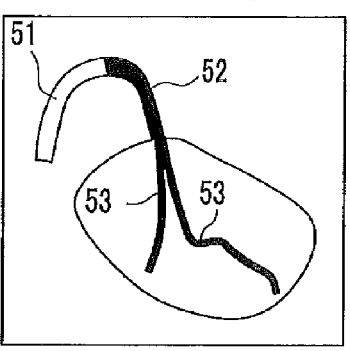

Display of recognizability

| Organ | recogniz-ability |
|---|---|
| · Bone(s) | × |
| · Ascending aorta | ○ |
| · Coronary artery | ○ |
| ⋮ | |

Judgment on recognition result

| Organ | Judgment |
|---|---|
| · Bone(s) | ✓ |
| · Ascending aorta | ✓ |
| · Coronary artery | ✓ |
| ⋮ | |

FIG.8A

Section A's slice image that is nearest section B

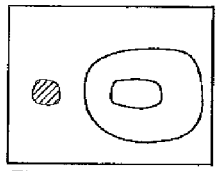

Display of recognizability

| Organ | recogniz-ability |
|---|---|
| ·Bone(s) | × |
| ·Ascending aorta | ○ |
| ·Coronary artery | × |
| ⋮ | |

Judgment on recognition result

| Organ | Judgment |
|---|---|
| ·Bone(s) | ✓ |
| ·Ascending aorta | |
| ·Coronary artery | ✓ |
| ⋮ | |

FIG.8B

Section B's slice image that is nearest section A

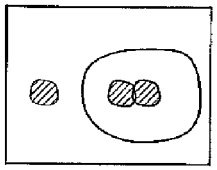

Display of recognizability

| Organ | recogniz-ability |
|---|---|
| ·Bone(s) | × |
| ·Ascending aorta | ○ |
| ·Coronary artery | ○ |
| ⋮ | |

Judgment on recognition result

| Organ | Judgment |
|---|---|
| ·Bone(s) | ✓ |
| ·Ascending aorta | |
| ·Coronary artery | ✓ |
| ⋮ | |

FIG.8C

Section B's slice image that is nearest section C

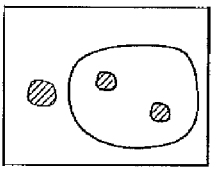

Display of recognizability

| Organ | recogniz-ability |
|---|---|
| ·Bone(s) | × |
| ·Ascending aorta | ○ |
| ·Coronary artery | ○ |
| ⋮ | |

Judgment on recognition result

| Organ | Judgment |
|---|---|
| ·Bone(s) | ✓ |
| ·Ascending aorta | |
| ·Coronary artery | ✓ |
| ⋮ | |

FIG.8D

Section C's slice image that is nearest section B

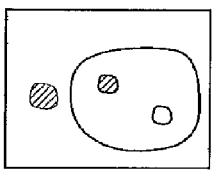

Display of recognizability

| Organ | recogniz-ability |
|---|---|
| ·Bone(s) | × |
| ·Ascending aorta | ○ |
| ·Coronary artery | ○ |
| ⋮ | |

Judgment on recognition result

| Organ | Judgment |
|---|---|
| ·Bone(s) | ✓ |
| ·Ascending aorta | |
| ·Coronary artery | |
| ⋮ | |

FIG.8E

Section C's slice image that is nearest section D

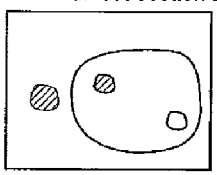

Display of recognizability

| Organ | recogniz-ability |
|---|---|
| ·Bone(s) | × |
| ·Ascending aorta | ○ |
| ·Coronary artery | ○ |
| ⋮ | |

Judgment on recognition result

| Organ | Judgment |
|---|---|
| ·Bone(s) | ✓ |
| ·Ascending aorta | |
| ·Coronary artery | |
| ⋮ | |

FIG.8F

Section D's slice image that is nearest section C

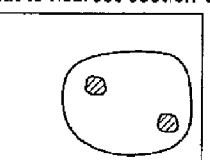

Display of recognizability

| Organ | recogniz-ability |
|---|---|
| ·Bone(s) | × |
| ·Ascending aorta | × |
| ·Coronary artery | ○ |
| ⋮ | |

Judgment on recognition result

| Organ | Judgment |
|---|---|
| ·Bone(s) | ✓ |
| ·Ascending aorta | ✓ |
| ·Coronary artery | ✓ |
| ⋮ | |

Display of recognition result

Modifying method 1

Portion of coronary artery

User's input

Modifying method 2

User's input

Three-dimensional region to be created

Specified two-dimensional region

Three-dimensional region to be created

Portion of coronary artery

Specified two-dimensional region

IMAGE PROCESSING METHOD, IMAGE PROCESSING APPARATUS AND PROGRAM

CROSS-REFERENCE TO RELATED APPLICATION

This application claims priority to International Application No. PCT/JP2010/071003, filed Nov. 25, 2010, which claims priority to Japanese Patent Application No. 2009-272007, filed Nov. 30, 2009 which are incorporated by reference as if fully set forth.

TECHNICAL FIELD

The present invention relates to an image processing method, image processing apparatus and program, and more specifically, to a technique of improving accuracy in recognizing images generated by visualizing medical image volume data that enables a three-dimensional representation by using a medical image processing algorithm.

BACKGROUND ART

Image diagnosis using medical image volume data (hereinafter referred to as the "volume data"), imaged by a medical imaging apparatus such as X-ray CT (X-ray Computed Tomography) or MRI (Magnetic Resonance Imaging: nuclear magnetic resonance imaging), has been using a plurality of medical image processing algorithms to visualize the volume data that have three-dimensional information and thereby produce images to be used as an aid for diagnosis.

Technical advancements in recent years have caused a significant increase in number of tomographic images (hereinafter referred to also as the "slice images") to be captured at once by a medical imaging apparatus, and thus in size of volume data to be output as the imaging result. In displaying images with use of medical image processing algorithms, it is very difficult to automate all the process of displaying images when safety and accuracy is taken into account. This makes it inevitable for surgeons and engineers to check and modify the images displayed through automation. However, manually checking the images lays a heavy burden on the surgeons and engineers when the volume data has a huge size. Accordingly, there is a demand for a more convenient and adaptable technique of checking and modifying the images displayed through automation in order to lighten the burden of manually checking the images.

Region growing is a main medical image processing algorithm employed for extracting a target region from volume data. In the region growing, a point or points called seed points are set manually or automatically, then pixel values of neighboring pixels of the set seed points are referred to determine if the pixel values fit set conditions, and if they do, the initial region or regions are grown from the set seed point or points to include the neighboring pixels.

The region growing is sensitive to where the seed points should be set and depending on the set conditions for the region growing, the region may be excessively grown even to areas which should not be extracted. A correcting method to be used in such a case is a reverse region growing method disclosed in Patent Document 1. The reverse region growing method is a method of return the grown region to its previous state by setting seed points again in the excessive areas and thereby shrinking the grown region.

A technique disclosed in Patent Document 2 is a method of obtaining an anatomical measurement value of a structure as a result of automatic extraction and then judging whether the value falls within a standard range thereby to automatically judge an appropriateness of the automatic extraction result.

A technique disclosed in Patent Document 3 is a method comprising automatically dividing an image into a plurality of basic regions according to feature amounts of pixels of the image, automatically integrating the plurality of basic regions into an integrated region based on features of the basic regions, automatically judging a kind of the integrated region, and specifying a position at which to correct a result of the judgment on the kind in order to correct the kind of a basic region or the integrated region.

PRIOR ART DOCUMENTS

Patent Documents

Patent Document 1: Japanese Patent No. 2874445
Patent Document 2: Japanese Unexamined Patent Publication No. 2009-95644
Patent Document 3: Japanese Unexamined Patent Publication No. 2008-259710

SUMMARY OF THE INVENTION

Problems that the Invention is to Solve

In recognizing a plurality of organs automatically in three-dimensional medical image data, then referring to the result of the automatic recognition, and reflecting user's inputs on the automatic recognition result, methods of displaying and modifying the automatic recognition result should be as easy and convenient as possible. The demand for such methods has been increasing more than ever these days when advancements in the field of medical imaging apparatus hardware require processing of greater size of medical image data.

However, the technique of the Patent Document 1 is sensitive to the setting of the seed points and has a problem that it is difficult to judge to what extent the region needs to be shrunk. The technique of Patent Document 2, in which the adequacy of the automatic extraction result is judged based on the standardized and averaged value, is inapplicable to some target organs having irregularities due to a lesion or a great extent of variations among individuals. The technique of Patent Document 3 requires the user to take time and trouble for making inputs to specify the position. Further, in this technique, since correction is made to the basic region as a unit obtained by the automatic division, it is difficult to extract a pixel from a region that is not recognized as a basic region at the time of the first division.

The present invention has been made to solve the above-mentioned problems of the conventional techniques, and it is an object of the present invention to provide an image processing method, image processing apparatus and program that enable easy modification of three-dimensional volume data which have undergone automatic organ recognition.

Means of Solving the Problems

To solve the above problems, a first invention provides an image processing apparatus comprising: an organ recognition algorithm executing unit that applies an organ recognition algorithm for recognizing a target organ to medical image volume data including data for a target organ to generate and output, as an organ recognition result, structural information on the target organ; and a recognition result displaying unit that displays the organ recognition result output from the organ recognition algorithm executing unit on a display device, the image processing apparatus using the predetermined image processing algorithm to perform an image processing of the medical image volume data, the image processing apparatus comprising: a recognition result judging unit that acquires, via an input device, judgment information as to whether or not the structural information is correct enough for the target organ to be properly recognized; and an organ recognition algorithm revising unit that acquires the judgment information from the recognition result judging unit, changes reference information on the target organ according to the acquired judgment information and modifies, if the reference information is changed, the organ recognition algorithm so as to recognize the target organ by using the changed reference information.

To solve the above problems, a second invention provides an image processing method for using an image processing apparatus, the image processing apparatus comprising: an organ recognition algorithm executing unit that applies an organ recognition algorithm for recognizing a target organ to medical image volume data including data for a target organ to generate and output, as an organ recognition result, structural information on the target organ; and a recognition result displaying unit that displays the organ recognition result output from the organ recognition algorithm executing unit on a display device, the image processing apparatus using the predetermined image processing algorithm to perform image processing of the medical image volume data, wherein the method comprises steps of: acquiring, via an input device, judgment information of whether or not the structural information is correct for the target organ; acquiring the judgment information from the recognition result judging unit; changing reference information on the organ according to the acquired judgment information; and, if the reference information is changed, modifying the organ recognition algorithm so as to recognize the target organ by using the changed reference information.

Effect of the Invention

The present invention provides an image processing method, image processing apparatus and program that enable easy modification of three-dimensional volume data which have undergone automatic organ recognition.

BRIEF DESCRIPTION OF THE DRAWINGS

FIG. 3 is a view showing examples of reference values used for the automatic organ recognition algorithm.

FIG. 5 shows an example of displayed images that represent a result of the automatic organ recognition performed by the automatic organ recognizing unit.

FIGS. 8A-8F are views showing an example of "display of recognizability" in a two-dimensional representation by the recognition result judging unit and of "judgment on recognition result".

MODE FOR CARRYING OUT THE INVENTION

Hereinafter, descriptions will be made of an image processing apparatus, image processing apparatus and program according to an embodiment of the present invention with reference to the drawings.

Figure 1:
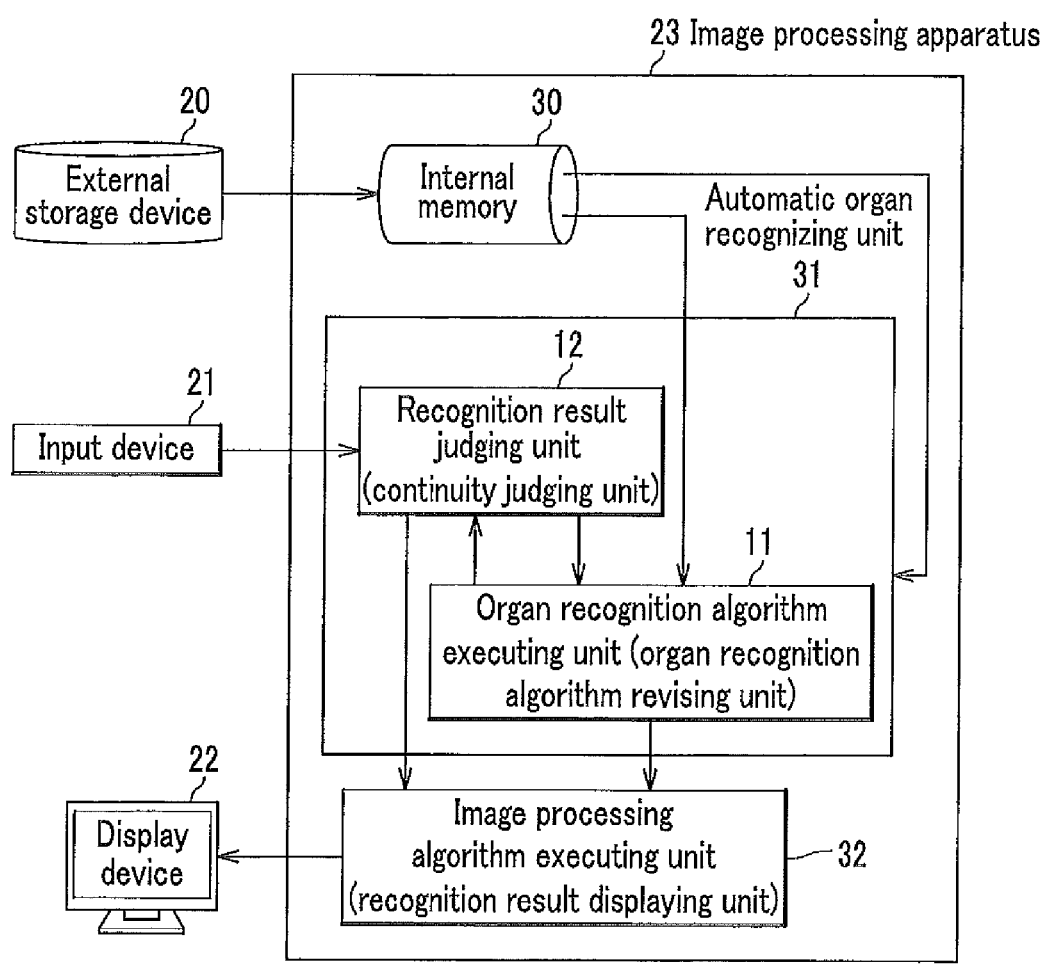
FIG. 1 is a system configuration diagram showing a configuration of an image processing apparatus according to an embodiment of the present invention.

FIG. 1 is a system configuration diagram showing a configuration of a system including an image processing apparatus according to an embodiment of the present invention.

As shown in FIG. 1, the system includes an image processing apparatus 23, an external storage device 20, an input device 21, and a display device 22. The image processing apparatus 23 processes volume data images captured by X-ray CT, MRI or the like. The external storage device 20 stores the captured volume data images. The input device 21 inputs results of judgment on a recognition result of the processed images. The display device 22 displays the processed images.

The image processing apparatus 23 includes an internal memory 30, an automatic organ recognizing unit 31 and an image processing algorithm executing unit 32. The automatic organ recognizing unit 31 includes a recognition result judging unit 12 and an organ recognition algorithm executing unit 11. The recognition result judging unit 12 judges whether or not an automatic organ recognition result is correct. The organ recognition algorithm executing unit 11 uses an automatic organ recognition algorithm to automatically recognize organs. The automatic organ recognizing unit 31 and the image processing algorithm executing unit 32 are embodied when programs are executed by a CPU (Central Processing Unit) or as dedicated circuits installed in the image processing apparatus 23. Further, other programs that allow the internal memory 30 and the image processing apparatus 23 to function are stored in a storage unit (not shown) which comprises a storage medium such as a RAM (Random Access Memory), a ROM (Read Only Memory), a HDD (Hard Disk Drive) or a flash memory.

Now, a description will be made of a process of automatic organ recognition up to the step thereof in which the automatic organ recognition result is displayed on the display device.

First, the volume data stored in the external storage device 20 are transferred to the internal memory 30. Next, the organ recognition algorithm executing unit 11 performs automatic organ recognition processing of the volume data stored in the internal memory 30 according to an automatic recognition instruction from the input device 21. Then, the organ recognition algorithm executing unit 11 transfers the automatic organ recognition result (structural information) to the image processing algorithm executing unit (recognition result displaying unit) 32 in order to display the automatic organ recognition result on the display device 22.

Based on judgment by the input device 21 on whether or not the automatic organ recognition result is correct, the recognition result judging unit 12 judges whether or not the automatic organ recognition result is correct. Then, the recognition result judging unit 12 transfers the judgment result to the organ recognition algorithm executing unit 11. The organ recognition algorithm executing unit 11 (organ recognition algorithm revising unit) reflects the judgment result transferred from the recognition result judging unit 12 on the automatic organ recognition algorithm and also transfers the recognition result to the image processing algorithm executing unit 32 in order to display the automatic recognition result on the display device 22.

Figure 2:
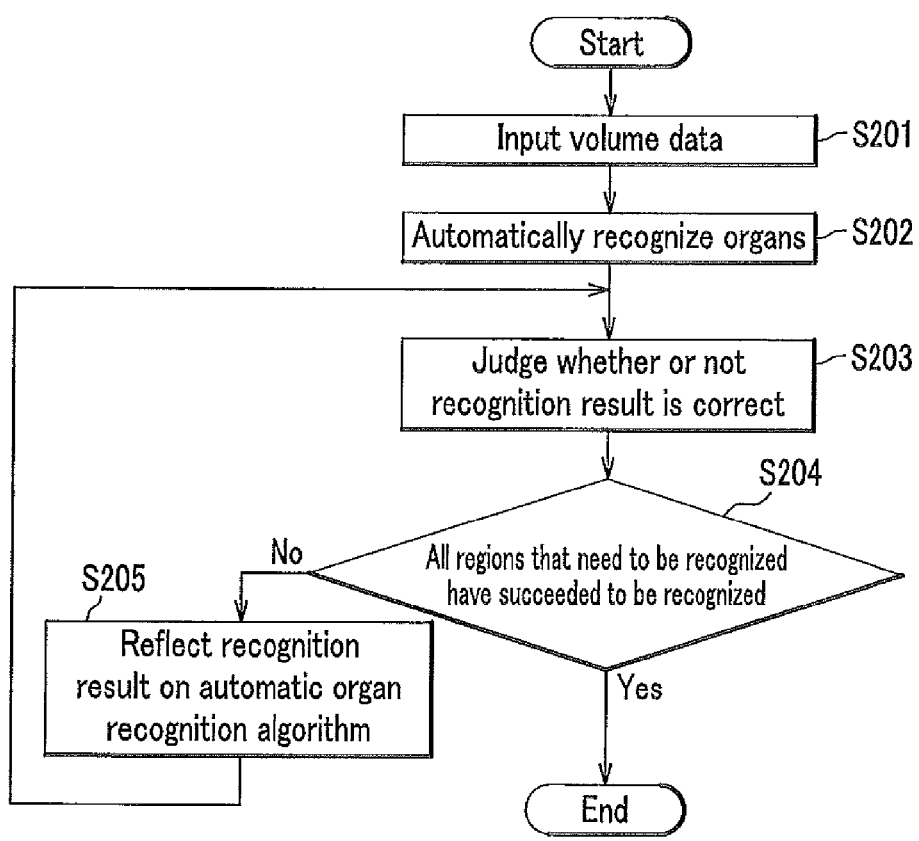
FIG. 2 is a flowchart showing an example of the organ recognition performed by an image processing apparatus.

FIG. 2 is a flowchart showing an example of the organ recognition performed in the image processing apparatus 23 (See FIG. 1 whenever it is necessary). First, the volume data stored in the external storage device 20 is input into the internal memory 30 of the image processing apparatus 23 (step S201). Then, the organ recognition algorithm executing unit 11 reads the volume data stored in the internal memory 30 and performs the automatic organ recognition processing by using the automatic organ recognition algorithm (step S202).

Next, the organ recognition algorithm executing unit 11 transfers the thus obtained organ recognition result to the image processing algorithm executing unit (recognition result displaying unit) 32 so that the organ recognition result is displayed on the display device 22 and it is judged via the input device 21 whether or not the recognition result is correct (step S203). If the judgment tells that any one of the regions that need to be recognized has failed to be recognized (No in step S204), the organ recognition algorithm executing unit 11 reflects the recognition result on the automatic organ recognition algorithm (step S205).

Here, there will be described an example of the case where the judgment on whether or not the automatic organ recognition result is correct is reflected on the automatic organ recognition algorithm. The automatic organ recognition algorithm refers to available ranges of values of the sizes (such as three-dimensional maximum distances) of a human organ. The available value ranges are able to be set based on general standards. However, some subjects' organ sizes may not fall within the available value ranges because organ sizes differ from person to person due to variations among individuals in physical size, age, sex, the like. In such a case, by relying on the fact that the same person's different organs have sizes correlated with each other, the automatic organ recognition algorithm can be updated to a more suitable one by changing the criteria for the automatic recognition of the organ, which so far fails to be recognized, by referring to values such as three-dimensional maximum distances of an organ already successfully recognized.

Then, again, the recognition result judgment is carried out according to the input from the input device 21. The above mentioned procedure is repeated, and the process is terminated when it is judged that all the regions that need to be recognized have been successfully recognized (Yes in step S204).

FIG. 3 is a view showing examples of reference values used for the automatic organ recognition algorithm.

Here, in a more specific example, it is assumed that the reference information made of information (1)-(7) as shown in FIG. 3 is used in an automatic organ recognition algorithm applied to the automatic recognition of the heart. In the information (1), the value of a diameter C of the coronary artery is represented as $C_{min}$-$C_{max}$, where $C_{min}$ and $C_{max}$ are respectively statistically probable minimum and maximum values of the diameter C of the coronary artery. In the information (2), the value of a diameter UA of the ascending aorta is represented as $UA_{min}$-$UA_{max}$, where $UA_{min}$ and $UA_{max}$ are respectively statistically probable minimum and maximum values of the diameter UA of the ascending aorta. In the information (3), the value of a diameter UB of the descending aorta is represented as $UB_{min}$-$UB_{max}$, where $UB_{min}$ and $UB_{max}$ are respectively statistically probable minimum and maximum values of the diameter UB of the descending aorta. In the information (4) and (5), a relation between $UA_{min}$ and $UB_{max}$ and a relation between $UA_{max}$ and $UB_{max}$ are expressed in terms of $F_a$ and $F_b$, respectively. In the information (6) and (7), the value of the diameter C of the coronary artery is expressed in terms of the diameter UA of the ascending aorta and the diameter UB of the descending aorta. Here, $F_a$, $F_b$, F, $F_d$ are parameters.

An initial value is assigned to each of $C_{min}$, $C_{max}$, $UA_{min}$, $UA_{max}$, $UB_{min}$, $UB_{max}$, $F_a$, $F_b$, $F_c$, $F_d$. The automatic organ recognition algorithm executing unit 11 performs automatic organ recognition using these initial values. Subsequently, if the recognition result judging unit 12 judges that any one or more of the coronary artery, the ascending aorta and the descending aorta have been successfully recognized and any one or more of them have failed to be recognized, the automatic organ recognition algorithm is updated by changing the rest of the values of $C_{min}$, $C_{max}$, $UA_{min}$, $UA_{max}$, $UB_{min}$ and $UB_{max}$ according to the minimum value or values and the maximum value or values of the successfully recognized organ or organs.

Figure 4A:
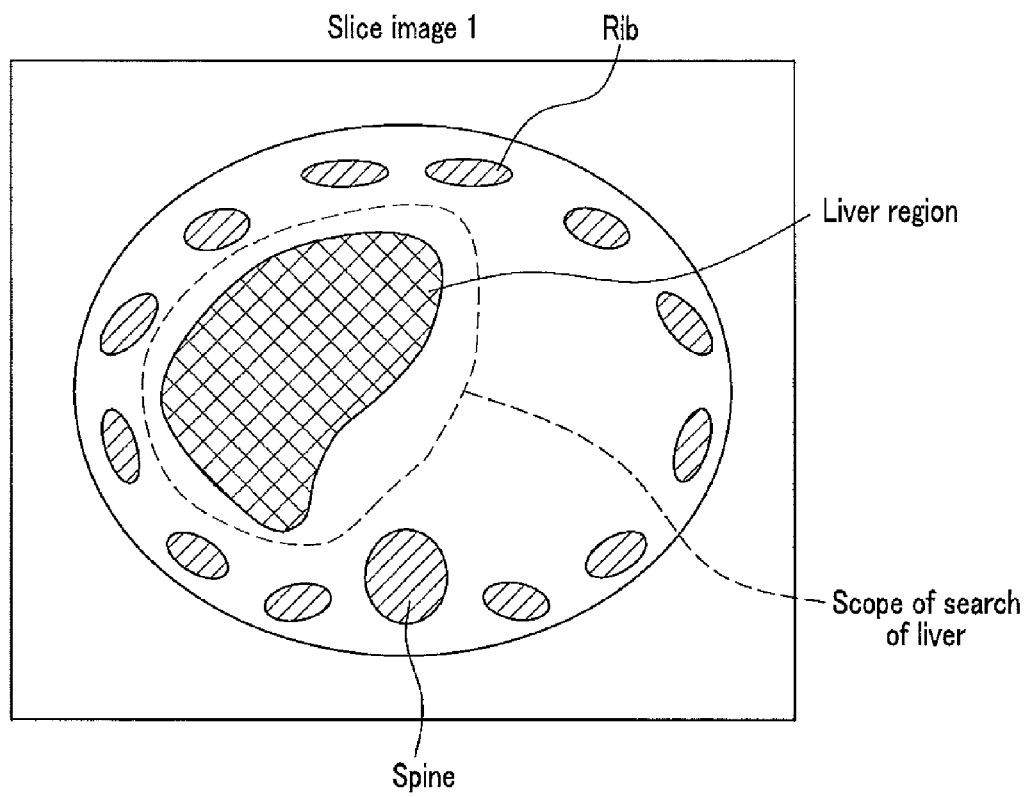
FIGS. 4A and 4B are views showing an example of a human body structure used for the automatic organ recognition algorithm.
Figure 4B:
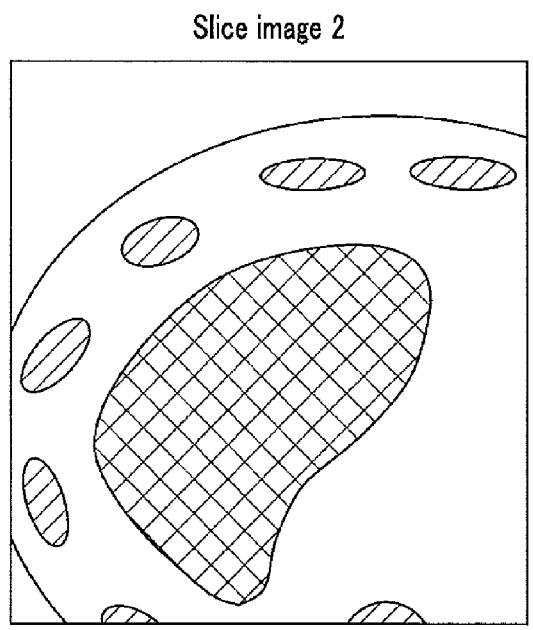

FIGS. 4A and 4B are views showing another example of the case where the recognition result judgment is reflected on the automatic organ recognition algorithm.

An example of the automatic organ recognition algorithm mentioned here is an algorithm for recognizing a liver region. As shown in an example of a human body structure used for the automatic organ recognition algorithm in FIG. 4A, a scope of search of the liver is set based on locations of the spine and the ribs, and the liver region is recognized within the set scope by using CT values. Here, for example, a recognition failure of, for example, the ribs makes it impossible to set the scope of search of the liver, and as a result, makes it impossible to correctly recognize the liver region.

For example, if captured CT image data is enlarged and reconstructed for easy observation of the liver region before the captured CT image data is used as input data, there are many cases where not all the spine or ribs are included in the volume data, creating a possibility of recognition failure of the bone regions, as in an example of automatic organ recognition failure shown in FIG. 4B. However, if a judgment that the bone regions have recognized is transferred via the input device 21 from the identification result determining unit 12, while the result of the automatic organ recognition is already on a display, which shows that the algorithm failed to recognize the spine, it is able to judge can be judged that there is no spine region in the volume data. As a result, for example, it becomes possible to judge that the volume data are for an enlarged view of the liver region and to estimate an approximate location of the liver region in the slice image, enabling such information to be reflected on the automatic organ recognition algorithm.

FIG. 5 shows an example of displayed images that represent a result of the automatic organ recognition performed by the automatic organ recognizing unit shown in FIG. 2. Here, the volume data is three-dimensionally displayed as the result of the organ recognition performed by the automatic organ recognizing unit 31. Different colors or textures are allocated to the regions that need to be recognized which when being automatically recognized are marked with those colors and textures. Further, a judgment on whether or not the organs have been correctly recognized as a result of the automatic organ recognition is displayed as "judgment on recognition result (judgment information)" separately from "display of recognizability". The "display of recognizability" is automatically displayed by the recognition result judging unit 12.

In the example shown in FIG. 5, a descending aorta 51, an ascending aorta 52 and a coronary artery 53 are shown.

A user judges whether or not the automatic organ recognition has succeeded by referring to the "display of automatic organ recognition result" and the "display of recognizability". In the example shown in FIG. 5, the checks "✓" are inserted for organs which are judged to have identified in the "judgment on recognition result" whereas no checks are inserted for organs which are judged to have failed to be identified.

For the region "bone(s)", the mark "x" indicative of being unrecognizable is shown in the "display of recognizability". On the other hand, when the user looks at the "display of automatic organ recognition result" which is a three-dimensional representation, he or she is able to judge that there is no bone region in the volume data and thus that the automatic organ recognition has been correctly performed. Accordingly, the user regards the identification of the region "bone(s)" as having succeeded and inserts the check "✓".

The user's judgment on the "display of recognizability" as described above is input via the input device 21 into the automatic organ recognizing unit 31. The automatic organ recognizing unit 31 reflects the user's judgment on the automatic organ recognition algorithm and executes the resulting automatic organ recognition algorithm. The thus obtained result is shown again as the automatic recognition result. The user performs the "judgment on recognition result" in the same manner as described above. If the user judges that all the organs mentioned in the "judgment on recognition result" have been successfully recognized, that is, if the user inserts the checks "✓" for all the organs in the "judgment on recognition result", the recognition result judging unit 12 judges that all the organs have been successfully recognized, and thus the procedure is ended.

The recognition result judging unit (recognition result automatic estimating unit) 12 may automatically estimate the "judgment on recognition result" that is as described above. For example, an organ or organs are not necessarily completely recognized as the result of the automatic organ recognition. Here, descriptions will be made of an example of how to input judgments into the "display of recognizability" and the "judgment on recognition result" not only in the case where the region of an organ is completely recognized and in the case where no region of an organ is recognized at all, but also in the case where only a part of the region of an organ is recognized.

Figure 6:
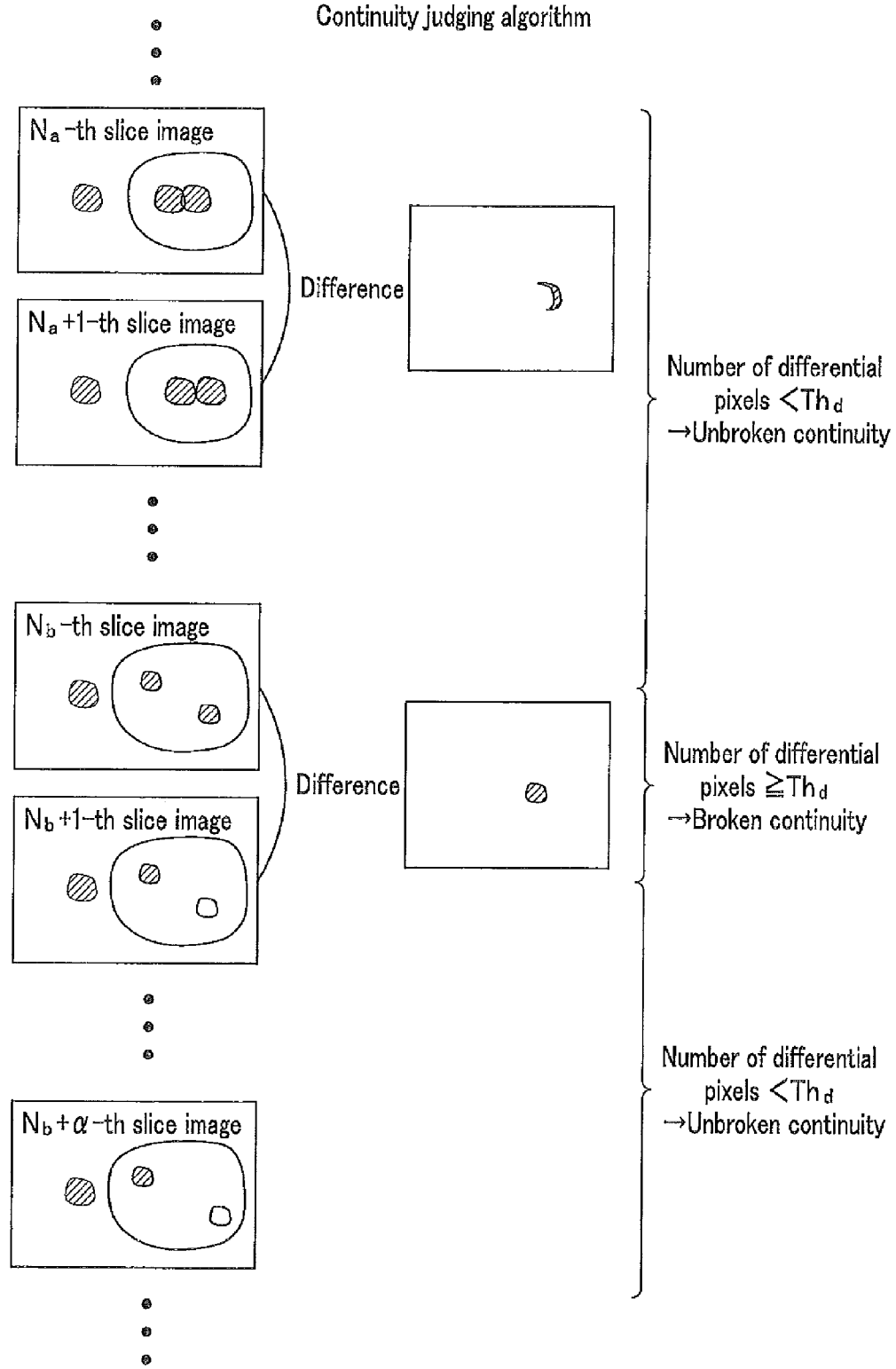
FIG. 6 is a view showing an example of application of a continuity algorithm to the recognition result judging unit.

FIG. 6 is a view showing an example of application of a continuity algorithm to the recognition result judging unit. The recognition result judging unit (continuity judging unit) 12 judges continuity for each of slice images obtained as the result of the automatic organ recognition. Here, it is estimated that there is a high possibility of recognition failure at and around a portion in which the continuity is broken, and a description will be made of a method in which a display is made per region in which the continuity is unbroken.

Different colors are respectively allocated to the regions of organs to be recognized, and when recognized, the pixels of each region are each marked with the color allocated to the region to which the recognized pixel belongs in order to reflect the recognition result on each slice image produced from the volume data and thereby obtain differential images between the adjacent slice images It is assumed that if the number of pixels in a differential image, that is, the number of differential pixels is less than a predetermined threshold value $Th_d$, the continuity between the adjacent slice images is unbroken whereas if the number of differential pixels is the same as or more than $Th_d$, the continuity between the adjacent slice images is broken.

As shown in FIG. 6, the number of differential pixels between an $N_a$-th slice image and an $N_a+1$-th slice image is less than $Th_d$ and thus it is determined that the continuity therebetween is unbroken. On the other hand, the number of differential pixels between an $N_b$-th slice image and an $N_b+1$-th slice image is the same or more than $Th_d$, and thus it is determined that the continuity therebetween is broken. This holds true for any differential images between the $N_b+1$-th slice image and an $N_b+\alpha$-th slice image. Further, the threshold value $Th_d$ may be assigned to each target organ. In such a case, the continuity is judged not based on the number of differential pixels in an overall slice image but based on the number of differential pixels of each target organ.

Figure 7:
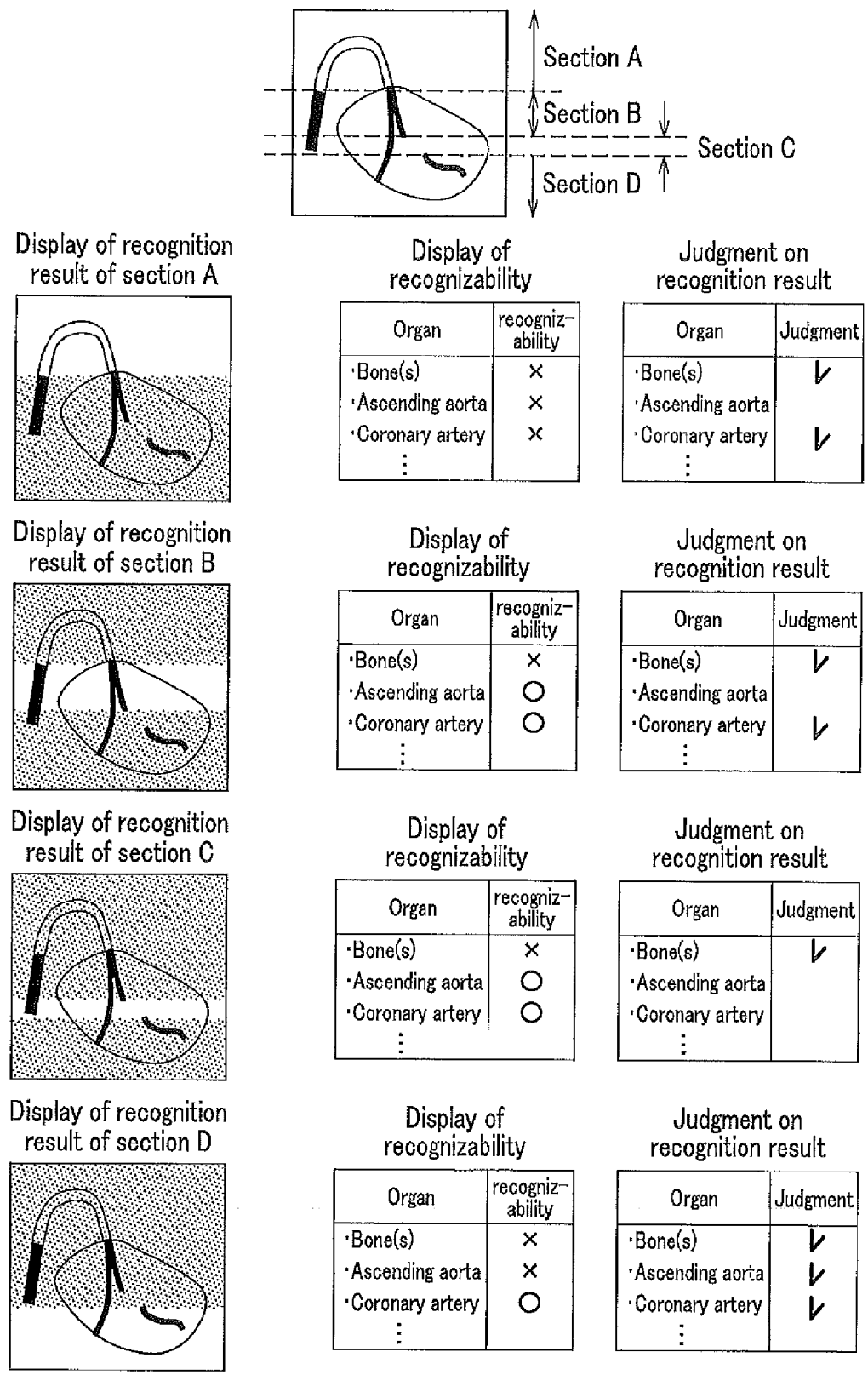
FIG. 7 is a view showing an example of "display of recognizability" in a three-dimensional representation by the recognition result judging unit and of how to carry out "judgment on recognition result".

FIG. 7 is a view showing an example of the "display of recognizability" in a three-dimensional representation by the recognition result judging unit and of how to carry out "judgment on recognition result". The continuity is judged by the recognition result judging unit (continuity judging unit) 12. FIG. 7 shows an automatic organ recognition result in three-dimensional representation of the heart region. Here, as the result of the automatic organ recognition, the coronary artery is shown with a part of it missing. The continuity in the example shown FIG. 7 is judged by the method of FIG. 6 to obtain images each divided into a section A (from a first slice image to a location where both the main artery region and the coronary artery region are recognized), a section B (from the location where both the ascending aorta 52 (See FIG. 5) and the coronary artery 53 region are recognized to a location where the coronary artery 53 region is started not to be recognized), a section C (from the location where the coronary artery 53 region is started not to be recognized to a location where the coronary artery 53 region is started to be recognized), and a section D (from the location where the coronary artery 53 region is started to be recognized to a last slice image).

The three-dimensional representation is made focusing on each of the sections A, B, C and D. Here, for the display of the section A, only the part that corresponds to the section A may be shown. However, as in the example shown in FIG. 7, the parts that correspond to the sections B, C and D may also shown as references.

In the "display of recognition result of section A", the "display of recognizability" that shows the result of the automatic organ recognition is shown to have the marks "x" indicative of being unrecognizable for the "bone(s)", the "ascending aorta 52" and the "coronary arteries 53". Since, of these, the "bone(s)" and the "coronary arteries 53" are able to be judged as being absent in the section A, the "judgment on recognition result" into which the user inputs his or her judgments is shown to have the checks "✓" for the "bone(s)" and the "coronary arteries 53" indicating the judgment that correct recognitions have been made.

In the "display of recognition result of section B", the "display of recognizability" that shows a result of the automatic organ recognition is shown to have the mark "x" for the "bone(s)" indicative of recognition failure thereof and the marks "○" for the "ascending aorta 52" and the "coronary arteries 53" indicative of recognition execution. Since, of these, the "bone(s)" are able to be judged as being absent in the section B and the "coronary arteries 53" are able to be judged as being present in the section B, the "judgment on recognition result" is shown to have the checks "✓" for the "bone(s)" and the "coronary arteries 53". The "ascending aorta 52" is absent in this region, and thus the "judgment on recognition result" is shown to have no check "✓". Here, the "descending aorta 51" is wrongly recognized as the "ascending aorta 52".

In the "display of recognition result of section C", the "display of recognizability" that shows a result of the automatic organ recognition is shown to have the mark "x" for the "bone(s)" indicative of recognition failure and the marks "○" for the "ascending aorta 52" and the "coronary arteries 53" indicative of recognition execution thereof. Since, of these, the "bone(s)" are able to be judged as being absent in the section C, the "judgment on recognition result" is shown to have the checks "✓" for the "bone(s)". For the "coronary arteries 53", there should be two "coronary arteries 53" intrinsically in this region, although one is missing to have the "coronary arteries 53" left blank in the "judgment on recognition result" without the check "✓" inserted. The "ascending aorta 52", which is absent in this region, is left blank in the "judgment on recognition result" without the check "✓" inserted. Here, the "descending aorta 51" is wrongly recognized as the "ascending aorta 52".

In the "display of recognition result of section D", the "display of recognizability" that shows a result of the automatic organ recognition is shown to have the marks "x" for the "bone(s)" and the "ascending aorta 52" indicative of recognition failure thereof and the mark "○" for the "coronary arteries 53" indicative of recognition execution thereof. Since, of these, the "bone(s)" and the "ascending aorta 52" are able to be judged as being absent in the section D, the "judgment on recognition result" into which the user inputs his or her judgments is shown to have the checks "✓" for the "bone(s)" and the "ascending aorta 52". Since the "coronary arteries 53" are able to be judged as being present in the section D, the "judgment on recognition result" is shown to have the check "✓" for the "coronary arteries 53".

The display of recognizability is made for each of the sections A, B, C and D, and the user inputs his or her judgments into the judgment on recognition result. Owing to this, even if a part of the regions that need to be recognized fail to be recognized, information on the rest that have been successfully recognized can be used for performing the automatic recognition again, enabling easy acquisition of more accurate recognition results.

FIGS. 8A-8F are views showing an example of "display of recognizability" in a two-dimensional representation by the recognition result judging unit and of "judgment on recognition result". There is shown an example of automatic organ recognition results each shown in a slice image in a two-dimensional representation at a location in which the continuity is broken, display of recognizability, and judgment on recognition result. In FIGS. 8A-8F, like FIG. 7, displays are made at locations in which the continuity is broken based on the assumption that recognition is likely to have failed at these locations of broken continuity. The recognition result judging unit (continuity judging unit) 12 judges the continuity and determines those locations by computation. However, unlike FIG. 7 which employs a three-dimensional representation, FIGS. 8A-8F employs representation in slice images. Here, there are shown slice images of the sections A, B, C and D at the locations where the adjacent sections border, that is, at the locations where the continuity is broken.

FIG. 8A shows a slice image of the section A at the location nearest the section B. The "display of recognizability" that shows a result of the automatic organ recognition is shown to have the mark "○" only for the "ascending aorta 52 (See FIG. 5)" whereas the "judgment on recognition result" shows that the "bone(s)" and the "coronary arteries 53" have been correctly recognized. FIGS. 8B and 8C show slice images of the section B that are at locations nearest the sections A and C, respectively. The "display of recognizability" is shown to have the marks "○" only for the "ascending aorta 52" and the "coronary arteries 53" whereas the judgment on "recognition result" shows that the "bone(s)" and the "coronary arteries 53" have been correctly recognized.

FIGS. 8D and 8E show slice images of the section C that are at locations nearest the adjacent sections B and D, respectively. The "display of recognizability" is shown to have the marks "○" only for the "ascending aorta 52" and the "coronary arteries 53" whereas the "judgment on recognition result" shows that the "bone(s)" have been correctly recognized. FIG. 8F shows a slice image of the section D at the location nearest the section C. The "display of recognizability" is shown to have the mark "○" only for the "coronary arteries 53" whereas the judgment on "recognition result" shows that the "bone(s)", the "ascending aorta 52" and the "coronary arteries 53" have been correctly recognized.

Three-dimensional representation has an advantage of configurations being instinctively grasped and a disadvantage of many overlapping portions being created depending on the angle, which makes it difficult to judge whether or not recognition results are correct. Representation in slice images confirms the judgment on which regions are recognized to what extent. Further, representation may be made every several slice images rather than on the continuity basis and the recognition results may be judged.

By referring to intrinsic configurations of organs rather than by judging the continuity, the recognition result judging unit 12 may judge which organs are likely to have failed to be recognized and preferentially display such regions in order to facilitate the user's manual input of his or her judgments into the judgment on the recognition result.

An example of the recognition of the coronary artery will be described. The coronary artery includes as main components the right coronary artery and the left main trunk. The left main trunk branches into the left anterior descending coronary artery and the left circumflex coronary artery. Accordingly, if the coronary artery is correctly recognized, two three-dimensional regions (the right coronary artery and the left main trunk with the following arteries) will be displayed with one of them (the left main trunk with the following arteries) having one widely branching-out part (the left anterior descending coronary artery and the left circumflex coronary artery).

By using the above-mentioned structure as a reference, the recognition result judging unit 12 automatically judges recognizability. If a recognized region has a structure that fails to conform to the standard structure thereof, the recognition result judging unit 12 judges that the region is likely to have failed to be recognized and transfers, to the image processing algorithm executing unit 32, information indicating that display of the region is to be preferred.

Further, the recognition result judging unit 12 may receive via the input device 21 not only the judgment on recognizability of organs that need to be recognized but also information on regions and sizes specified by the user.

Figure 9A:
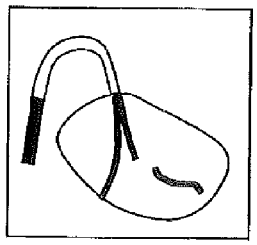
FIGS. 9A-9E are views showing examples of a case where the user's input other than judgment on recognition result is reflected on an automatic recognition algorithm.

FIGS. 9A-9E are views showing examples of a case where the user's input other than his or her judgment on recognizability is reflected on an automatic recognition algorithm. FIG. 9A is a view showing a result of the automatic organ recognition. As shown in FIG. 9A, the organs are recognized as having a part of the coronary artery 53 (FIG. 5) missing. Here, the user estimates the location and size of the insufficiently recognized part, that is, the missing region of the coronary artery 53, and inputs information thereon to update the automatic organ recognition algorithm.

Figure 9B:
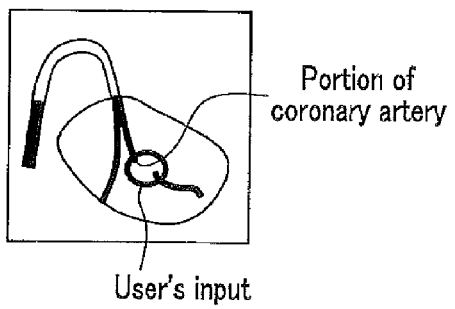

Specific examples will be described with reference to FIGS. 9B-9E. FIGS. 9B-9D shows a modifying method 1. In the modifying method 1, the user employs the input device 21 such as a mouth, a cursor or the like to draw a line and thereby specify a region estimated to be insufficiently recognized. Here, since the volume data is three-dimensional data, it is necessary to create a three-dimensional region using the line drawn by the user as an outline of a two-dimensional region. FIGS. 9C and 9D are views showing examples of how to create the three-dimensional region from the two-dimensional region. In a method of FIG. 9C, the three-dimensional region is created as a cylindrical region by specifying a two-dimensional region and extending a plane at right angles to the specified two-dimensional region in a direction upright relative to a plane of projection in a three-dimensional representation. In a method of FIG. 9D, the three-dimensional region is a portion of the cylindrical region including portions of already recognized coronary artery 53 used as a reference for designating the portion. Information on the thus specified three-dimensional region is reflected on the automatic organ recognition algorithm used for the coronary artery 53. Here, the recognition is made on the presumption that the specified three-dimensional region includes the unrecognized coronary artery 53 region and that it should be connected to the portions included in the specified three-dimensional regions. The newly recognized region is added to the already recognized coronary artery 53 regions in order to update the automatic organ recognition algorithm.

Figure 9E:
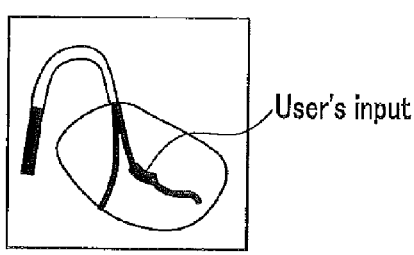
Figure 9C:
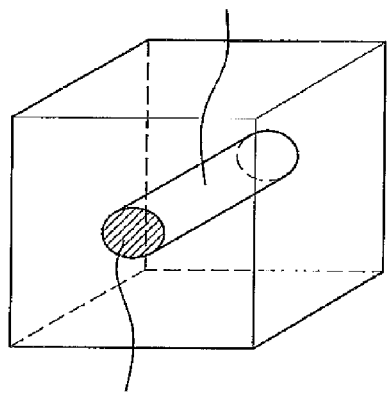
Figure 9D:
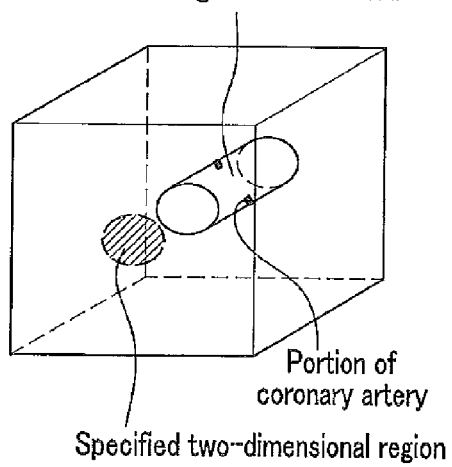

FIG. 9E shows a modifying method 2. In the modifying method 2, if a part of the coronary artery 53 region is estimated to be missing, the user draws a line from one end of the missing part to the other end, both ends being in the already recognized coronary artery 53 regions, by using the input device 21 such as a mouth, a cursor or the like, thereby to input the length of the line and the locations of those ends. When the thus obtained information is reflected on the automatic organ recognition algorithm, the algorithm is updated so that the coronary artery 53 can be recognized as including a region of a pipe shape having a diameter determined by estimating the diameters of blood vessels of the respective already recognized coronary artery 53 regions and referring to the estimated diameters thereof.

As described above, in cases as shown in display of the recognition result of FIG. 9A, the user is able to easily determine that the coronary artery 53 has a missing part and an approximate location of the missing part when viewing the three-dimensional representation. Accordingly, by making inputs as in the modifying methods 1 and 2, organs are able to be readily recognized again.

As described above, the present invention makes it possible to execute an algorithm for automatically recognizing a plurality of organs on three dimensionally visualizable volume data in order to subsequently visualize the automatic recognition results three- or two-dimensionally in an easy-to-understand manner, and also facilitate a modification of the displayed recognition results.

DESCRIPTION OF REFERENCE NUMERALS 11 organ recognition algorithm executing unit (organ recognition algorithm revising unit)
12 recognition result judging unit (recognition result automatic estimating unit, continuity judging unit)
20 external storage device
21 input device
22 display device
23 image processing apparatus
30 internal memory
31 automatic organ recognizing unit
32 image processing algorithm executing unit (recognition result displaying unit)
51 descending aorta
52 ascending aorta
53 coronary artery (coronary artery)

The invention claimed is:

1. An image processing apparatus comprising:
an organ recognition algorithm executing unit that applies an organ recognition algorithm for recognizing a target organ to medical image volume data including data for a target organ to generate and output, as an organ recognition result, structural information on the target organ; and
a recognition result displaying unit that displays the organ recognition result output from the organ recognition algorithm executing unit on a display device,
the image processing apparatus using the predetermined image processing algorithm to perform an image processing of the medical image volume data,
the image processing apparatus comprising:
a recognition result judging unit that acquires, via an input device, judgment information as to whether or not the structural information is correct enough for the target organ to be properly recognized; and
an organ recognition algorithm revising unit that acquires the judgment information from the recognition result judging unit, changes reference information on the target organ according to the acquired judgment information and modifies, if the reference information is changed, the organ recognition algorithm so as to recognize the target organ by using the changed reference information;
wherein
the recognition result judging unit comprises a continuity judging unit that acquires a differential image indicating a difference in a number of pixels between adjacent tomographic images corresponding to the medical image volume data generating the structural information on a portion of the target organ, the portion having been judged to be a recognized region, to judge continuity between the tomographic images based on the number of pixels in the differential image, and wherein
the recognition result displaying unit performs a two- or three-dimensional visualization of the region judged to be continuous by the continuity judging unit.

2. The image processing apparatus of claim 1, wherein
the recognition result judging unit comprises a continuity judging unit that acquires a differential image indicating a difference in a number of pixels between adjacent tomographic images corresponding to the medical image volume data generating the structural information on a portion of the target organ, the portion having been judged to be a recognized region, to judge continuity between the tomographic images based on the number of pixels in the differential image.

3. The image processing apparatus of claim 1, wherein
when the recognized region actually includes an unrecognizable region, the organ recognition algorithm executing unit modifies the unrecognizable region by using the input device to reflect the results of the modification of the unrecognizable region on the organ recognition algorithm.

4. An image processing method for using an image processing apparatus, the image processing apparatus comprising:

an organ recognition algorithm executing unit that applies an organ recognition algorithm for recognizing a target organ to medical image volume data including data for a target organ to generate and output, as an organ recognition result, structural information on the target organ; and a recognition result displaying unit that displays the organ recognition result output from the organ recognition algorithm executing unit on a display device, the image processing apparatus using the predetermined image processing algorithm to perform image processing of the medical image volume data, wherein the method comprises steps of:

acquiring, via an input device, judgment information of whether or not the structural information is correct for the target organ;

acquiring the judgment information from the recognition result judging unit;

changing reference information on the organ according to the acquired judgment information; and, if the reference information is changed, modifying the organ recognition algorithm so as to recognize the target organ by using the changed reference information;

wherein the recognition result judging unit comprises the step of generating tomographic images of an organ judged to be a recognized region by using the structural information, to acquire a differential image indicating a difference in a number of pixels between the adjacent tomographic images for judging continuity between the tomographic images based on the number of pixels in the differential image, and wherein the image processing algorithm executing unit performs a two- or three-dimensional visualization of the region judged to be continuous by the continuity judging unit.

5. The image processing method of claim 4, wherein the image processing method comprises the step of generating tomographic images of an organ judged to be a recognized region by using the structural information, to acquire a differential image indicating a difference in a number of pixels between the adjacent tomographic images for judging continuity between the tomographic images based on the number of pixels in the differential image.

6. The image processing method of claim 4, wherein when the recognized region actually includes an unrecognizable region, the organ recognition algorithm executing unit modifies the unrecognizable region by using the input device to reflect the results of the modification of the unrecognizable region on the organ recognition algorithm.

7. A program residing in a non-transitory computer readable medium allowing a computer to execute an image processing method as cited in claim 4.

* * * * *